United States Patent [19]

Chiquiar-Arias

[11] 3,998,224
[45] Dec. 21, 1976

[54] DISPOSABLE SELF-DESTRUCTIBLE SYRINGES WHICH RENDER THEMSELVES UNREUSABLE

[76] Inventor: Marcelo Chiquiar-Arias, P.O. Box 11-385, Mexico City 11, Mexico

[22] Filed: Apr. 6, 1976

[21] Appl. No.: 674,263

Related U.S. Application Data

[62] Division of Ser. No. 474,283, May 29, 1974, Pat. No. 3,951,146.

[30] Foreign Application Priority Data

Aug. 15, 1973 Mexico.......................... 145570

[52] U.S. Cl. .................. 128/218 R; 128/218 P
[51] Int. Cl.² ............................ A61M 5/00
[58] Field of Search ..... 128/218 R, 218 P, 218 PA, 128/218 C, 215, 261, 234; 222/541; 401/198; 30/90.1, 90.4, 123 R

[56] References Cited

UNITED STATES PATENTS

| | | | |
|---|---|---|---|
| 2,619,087 | 11/1952 | Oclassen .................. | 128/234 X |
| 2,724,385 | 11/1955 | Lockhart ................... | 128/234 X |
| 2,752,920 | 7/1956 | Kurkjian ................... | 128/261 |
| 2,764,981 | 10/1956 | Helmer et al. ............ | 128/218 C |
| 2,833,280 | 5/1958 | Hein, Jr. .................. | 128/218 D |
| 2,882,899 | 4/1959 | Nogier et al. ............. | 128/218 P |
| 3,220,413 | 11/1965 | Sunnen ..................... | 128/261 |
| 3,667,657 | 6/1972 | Chiquiar-Arias .......... | 128/218 R X |
| 3,951,146 | 4/1976 | Chiquiar-Arias .......... | 128/218 R |

FOREIGN PATENTS OR APPLICATIONS

| | | | |
|---|---|---|---|
| 1,257,067 | 2/1961 | France ..................... | 128/218 P |
| 107,080 | 4/1971 | Mexico .................... | 128/218 P |
| 268,694 | 5/1951 | Switzerland .............. | 128/218 P |

Primary Examiner—John D. Yasko
Attorney, Agent, or Firm—Ladas, Parry, Von Gehr, Goldsmith & Deschamps

[57] ABSTRACT

This invention refers to disposable syringe containers used for injection which destroy themselves and render themselves unreusable, characterized principally in that they are made of a material which can be cut or perforated with the normal injecting movement of the piston in the syringe, thus destroying them and which have parts which engage the piston to the cylinder or to the injection needle after the first use and prevent any further use of the syringe.

5 Claims, 3 Drawing Figures

3,998,224

DISPOSABLE SELF-DESTRUCTIBLE SYRINGES WHICH RENDER THEMSELVES UNREUSABLE

REFERENCES TO OTHER APPLICATION

The present application is a divisional of my Pat. Application No. 474,283 filed May 29, 1974 now U.S. Pat. No. 3,951,146.

BACKGROUND OF THE INVENTION

This invention is designed to solve not only the problem of preventing contamination caused by disposable syringes if they are reused by the users, since this is a current problem of world interest, this problem is completely solved with the syringes which render themselves unreusable, which are the subject of the aforementioned Patent Application, but this invention also provides the solution to the problem of the possible reuse of syringes by drug addicts, a problem which was not completely solved with the aforementioned syringes which rendered themselves unreusable.

The improvements set forth in this invention make the use of the syringes more effective and easier and prevent their possible reuse, even in a partial manner, as well as preventing the possible reuse of the injection needle. The aforementioned syringes could have their needles reused inasmuch as regular needles were used. For this reason, one of the aspects of this invention is to prevent the possible reuse of the needles.

My U.S. Pat. No. 3,667,657 shows a prefilled syringe in which a non-retractable knife destroys the syringe on use. There are some injectable solutions which cannot be stored for a given amount of time in containers made of material which can be cut with a blade, such as plastic or similar materials. For this reason there is a necessity for a syringe for these types of solutions which can be filled without the blade cutting the cylinder at the time that the solution is extracted from its container in the process of filling the syringe. My Mexican Patent No. 107,080 shows attaching a resiliently mounted knife to one of the sides of the flaps of the piston rod.

In view of the fact that in most of the foregoing embodiments, drug addicts can refill, even with a small amount of solution, the destroyed syringe due to the small part of the syringe which is not cut and which corresponds to the size of the piston of the plunger, this invention furthermore includes the following aspects that solves this and other problems.

In accordance with the present invention there is provided a disposable syringe which renders itself nonreusable which comprises a rigid cylinder coupled at one end to a bottom wall with an opening for the exit of the solution to be injected, and having the other end open, said end being integrally coupled to support flanges which extend outwardly and perpendicularly to the axis of the cylinder, and a plunger with a piston at the extreme end coupled to the cylinder, the piston having at least one punch rod which extends parallel to the longitudinal axis of the cylinder and is adapted to engage or puncture the bottom wall of said cylinder so as to prevent reuse.

One of the embodiments of this aspect of the invention, has in the forward part of the piston, a needle or pin which coincides with a weakened portion or groove made in the forward part of the cylinder without fully puncturing the wall of the same, in which case, when the solution is injected by the user and the piston reaches the end of its movement, the cylinder will be fully punctured in the said weakened section, preventing a possible reuse, however small it might be, of the syringe inasmuch as the syringe will be completely unusable. Of course this kind of destruction could be combined with the cutting blade which is outlined in the above models.

Another embodiment which solves the problem mentioned above has in the center and in the forward part of the piston a ribbed and toothed projection, or any other kind of mechanism which would jam when inserted into the needle on the first application of the solution, and it would stick in the ribbed part of the needle with which it would coincide, jamming the plunger with the needle, making any further reuse impossible. This embodiment could also be combined with the cutting blade as in my above mentioned application and would include a stop near the extreme end of the cylinder of the syringe container in order to prevent destruction of the syringe when being assembled before the first application, preventing the pin and the jamming mechanism from making the syringe unworkable prematurely.

These and other objectives to be obtained for the use of this invention will be better understood and appreciated by the reading of the following description which refers to the drawings of the preferred embodiment of the present invention.

DETAILED DESCRIPTION OF THE INVENTION

Figure 1:
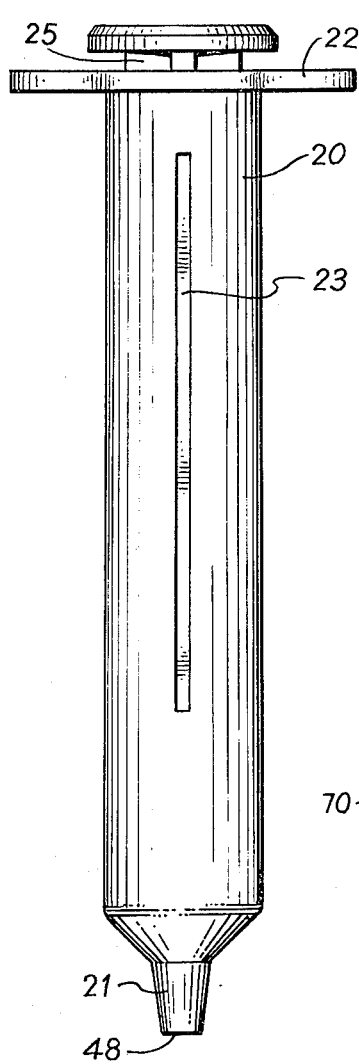
FIG. 1 is a vertical elevational view of a model of one embodiment of the invention of my above Application No. 474,283 for disposable or empty syringes with cutting blades elastically supported by springs located on the inside of the slots made in one flap of the plunger of the syringe.
Figure 3:
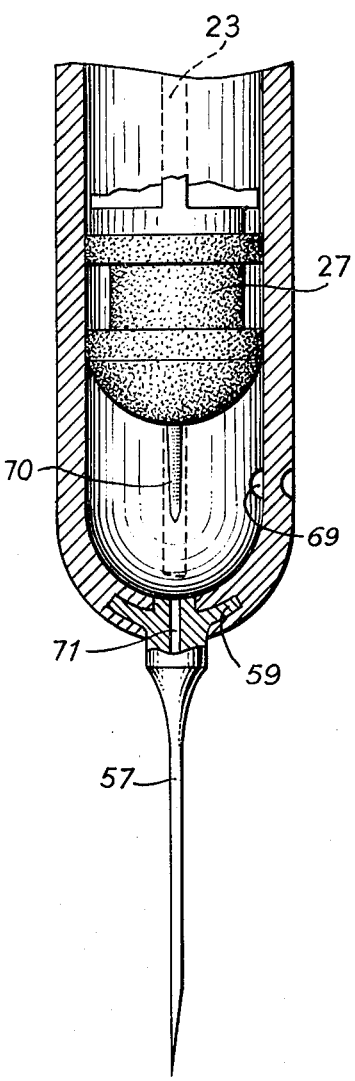
FIG. 3 is a view similar to FIG. 2 in which the pin is used in the center and forward section of the piston, which pin is ribbed or slotted and jams with the rearward orifice of the needle.
Figure 2:
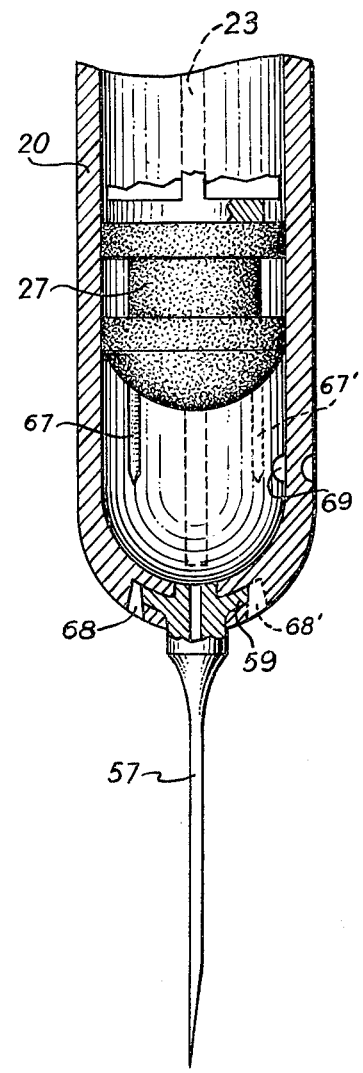
FIG. 2 is a conventional longitudinal sectional view showing an embodiment of the disposable syringe of this invention with a puncturing pin located in the forward section of the piston of the syringe and which coincides with a weakened section of the forward part of the cylinder of the same which allow the nonreusability of the syringe once the piston reaches the end of its movement during a complete injection of the solution. The dotted lines show the weakened sections of the cylinder which will be cut with the blade of the foregoing models inasmuch as both systems can be combined to increase the efficiency of the non-reusability of the syringes.

As related to the Figures, the improved syringe which is the subject of this invention is constructed according to the embodiments illustrated in FIGS. 1 to 3, with a cylinder 20 made of a material which can be cut by a knife, such as plastic or some similar material, and which has at one of its extreme ends a pivot 21 and at the other, projecting itself perpendicularly from its longitudinal axis, a pair of flanges 22, almost opposite, which function as supports for the user; cylinder 20, also includes a slot or longitudinally weakened section 23 on the inside of the cylinder 20, almost the whole length of the cylinder; the slot or opening 23, which is a part of the invention of my above application is not present in the cylinder 20 of the present invention, but FIG. 1 is presented to show the exterior of the syringe of the present invention.

The plunger of the syringe has some flaps which are practically in the shape of a cross. As described in my above application, at one of its extreme ends the plunger has a circular disk and at its other extreme end a piston with some annular sealing bosses. Said cylinder has in its inside surface some protuberance, which may be formed by simple pressure applied to the outside wall of the cylinder with a hot punch which will form the desired ledge which will act as a stop against one of the annular sealing bosses, limiting the backward movement of the plunger or piston, and at the same time functioning as guides for the flaps to prevent the plunger from turning.

FIG. 2 shows an embodiment applicable to syringe containers, prefilled syringes and empty syringes of any of the aforementioned types, as for example that which is used with needle 57, embedded in the material of which the cylinder is made. The piston 27 has in its forward section a punch 67 aimed at the extreme front part of the cylinder 20 parallel to the longitudinal axis of the syringe and coinciding with a perforation 68 made in the outside forward section of said cylinder 20, which weakens the wall of the same, by means of which, once the movement of the piston 27 is completed in the injection process, the punch 67 will totally perforate the forward section of the cylinder which has already been weakened by the perforation 68 and the result will be that the syringe cannot be refilled in any way; this destructive process for the syringe may be combined with the cutting blade which will cut the cylinder as shown by the dotted lines 23 which indicate the slots made in the outside of the cylinder 20 when this model of empty syringe is used and which includes a forward stop 69 which will tell the person assembling the syringe how far he can extend the piston 27 without having the punch 67 perforate the cylinder through the opening 68, which will obviously form an initial vacuum in the syringe when the same is filled with the solution to be injected and which should be eliminated from the syringe before the user begins the injection operation. Instead of a single perforation 68 there can be provided a weakened portion in the form of a ring surrounding skirt 59, whereby the cross-section of one side of the ring is shown by cut out portion 68 and the other side by cut portion 68' as shown by dotted lines in FIG. 2. In this modification it is not necessary to have the flaps 25 of the piston guided by a protuberance to prevent the piston from rotating since the punch 67 can hit anywhere within the cut-out ring 68–68'.

An embodiment which is very similar to the foregoing is shown in FIG. 3, the difference being that in place of the piston 27 a ribbed and toothed pin rod 70 is placed in the forward central section of the piston 27, which when introduced into the needle 57 will jam in the ribs or teeth 71, preventing the removal of the plunger from the syringe.

I claim:

1. A disposable syringe which renders itself non-reusable which comprises a rigid cylinder coupled at one end to a bottom wall with an opening for the exit of the solution to be injected, and having the other end open, said end being integrally coupled to support flanges which extend outwardly and perpendicularly to the axis of the cylinder, and a plunger with a piston at the extreme end coupled to the cylinder, the piston having at least one punch rod which extends parallel to the longitudinal axis of the cylinder and is adapted to engage or puncture the bottom wall of said cylinder so as to prevent reuse.

2. A disposable syringe according to claim 1, in which there is a weakened portion extending only partially through the bottom wall of said cylinder, the punch being aligned with said bottom wall, there being a stop in the side wall of the cylinder near the forward part thereof, said stop being adapted to prevent the piston from moving unintentionally into contact with the inside surface of the forward wall of said cylinder during assembling.

3. A disposable syringe according to claim 2, in which the weakened portion is a ring extending about the needle.

4. A disposable syringe according to claim 2, in which the weakened portion is a perforation, the piston rod being adapted to be guided during its movement so as to prevent its rotation about its axis.

5. A disposable syringe according to claim 1, in which the rod coincides with the position of the needle on the bottom wall of the cylinder, there being a plurality of serrations on said rod and also serrations on the inside of an orifice of the needle, whereby coupling of the rod in the orifice of the needle prevents further use.

* * * * *